United States Patent [19]

Woodruff et al.

[11] Patent Number: 4,888,347

[45] Date of Patent: Dec. 19, 1989

[54] USE OF SPECIFIC N-METHYL-D-ASPARTATE RECEPTOR ANTAGONISTS IN THE PREVENTION AND TREATMENT OF NEURODEGENERATION

[75] Inventors: Geoffrey N. Woodruff, Braughing; Erik H. F. Wong; John A. Kemp, both of Hertford, all of England

[73] Assignee: Merck Sharp & Dohme Limited, Hoddesdon, England

[21] Appl. No.: 946,262

[22] Filed: Dec. 24, 1986

[30] Foreign Application Priority Data

Jan. 14, 1986 [GB] United Kingdom ................. 8600783

[51] Int. Cl.$^4$ ....................... A61K 31/44; A61K 31/40
[52] U.S. Cl. ..................................... 514/289; 514/410
[58] Field of Search ......................... 514/294, 289, 411

[56] References Cited

U.S. PATENT DOCUMENTS

| | | | |
|---|---|---|---|
| 4,064,139 | 12/1977 | Anderson et al. | 514/964 |
| 4,374,838 | 2/1983 | Anderson et al. | 514/289 |
| 4,399,141 | 8/1983 | Anderson et al. | 514/294 |
| 4,657,899 | 4/1987 | Rzeszotarski et al. | 514/113 |

OTHER PUBLICATIONS

Goodman and Gillman, *The Pharmacological Basis of Therapeutics*, 5th ed. (1975) pp. 201–211 and 220–221.
The Lancet, pp. 140–143 (1985) Schwarcz et al.

*Primary Examiner*—Douglas W. Robinson
*Assistant Examiner*—Richard Kearse
*Attorney, Agent, or Firm*—William H. Nicholson; Joseph F. DiPrima

[57] ABSTRACT

Specific N-methyl-D-aspartate receptor antagonists are useful in the prevention and treatment of neurodegeneration in various pathological states.

8 Claims, No Drawings

USE OF SPECIFIC N-METHYL-D-ASPARTATE RECEPTOR ANTAGONISTS IN THE PREVENTION AND TREATMENT OF NEURODEGENERATION

SUMMARY OF THE INVENTION

This invention is concerned with specific antagonists of N-methyl-D-aspartate (NMDA) receptors which are useful in the prevention and/or treatment of neurodegeneration in pathological conditions such as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Olivo-ponto-cerebellar atrophy, anoxia such as from drowning, spinal cord injury and poisoning by exogenous NMDA poisons (e.g. some forms of lathyrism).

BACKGROUND OF THE INVENTION

Excessive excitation by neurotransmitters can cause the degeneration and death of neurons. It is believed that this excitotoxic action is responsible for neuronal loss in stroke, cerebral palsy, cerebral ischaemia, perinatal asphyxia, epilepsy, ageing and Alzheimer's disease, Huntington's chorea and other chronic neurodegenerative disorders.

There are no specific therapies for these neurodegenerative diseases, but compounds acting specifically to antagonise excitatory neurotransmission at NMDA receptors could offer a novel therapeutic approach to these disorders (Schwarcz, R and Meldrum B, *The Lancet*, 140 (1985)).

Now with the present invention, there is provided a method of prevention and/or treatment of neurodegeneration in the aforementioned pathological conditions by the administration of specific, orally active NMDA receptor antagonists.

DETAILED DESCRIPTION OF THE INVENTION

The novel method of treatment of neurodegeneration of this invention comprises the administration to a patient in need of such treatment with an effective amount of an N-methyl-D-aspartate (NMDA) receptor antagonist.

The NMDA receptor antagonists useful in the novel method of treatment of this invention include compounds of the following structural formulae which are described in U.S. Pat. Nos. 4399141; 4374838 and 4064139, the disclosures of which are incorporated herein by reference:

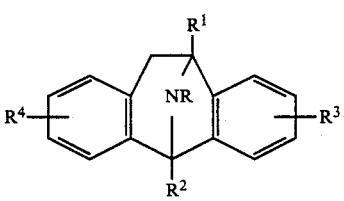

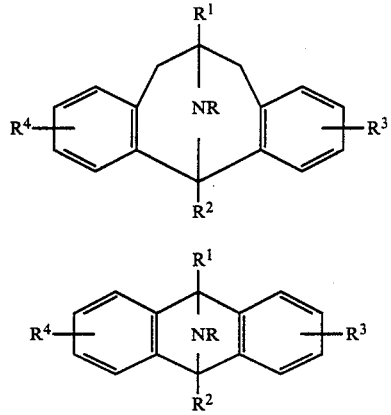

or a pharmaceutically acceptable salt thereof, wherein R is
(1) hydrogen,
(2) $C_{1-5}$ alkyl, preferably methyl or ethyl,
(3) $C_{2-5}$ alkenyl, preferably vinyl or allyl,
(4) phenyl (or substituted phenyl)-($C_{1-3}$ alkyl)-, preferably benzyl or substituted benzyl wherein the substituent is halo such as fluoro, chloro or bromo,
(5) $C_{3-6}$ cycloalkyl, preferably cyclopropyl or cyclohexyl,
(6) ($C_{3-6}$ cycloalkyl)-($C_{1-3}$ alkyl), or
(7) di($C_{1-5}$ alkyl)amino-($C_{1-5}$ alkyl), especially dimethylaminopropyl;

$R^1$ is
(1) hydrogen,
(2) $C_{1-5}$ alkyl, preferably methyl or ethyl
(3) $C_{2-5}$ alkenyl, preferably vinyl or allyl
(4) phenyl-($C_{1-3}$ alkyl), preferably benzyl,
(5) $C_{3-6}$ cycloalkyl, preferably cyclopropyl or cyclohexyl, or
(6) ($C_{3-6}$ cycloalkyl)-($C_{1-3}$ alkyl), $R^2$ is
(1) $C_{1-5}$ alkyl, preferably methyl or ethyl
(2) $C_{3-5}$ alkenyl, preferably allyl,
(3) phenyl-($C_{1-3}$ alkyl), preferably benzyl,
(4) ($C_{3-6}$ cycloalkyl)-($C_{1-3}$ alkyl),
(5) di($C_{1-5}$ alkyl)amino-($C_{1-5}$ alkyl), especially dimethylaminopropyl; or
(6) $C_{2-3}$ hydroxyalkyl, preferably hydroxyethyl; and $R^3$ and $R^4$ are independently,
(1) hydrogen
(2) halogen, such as chloro, bromo, fluoro or iodo,
(3) $C_{1-5}$ alkoxy, preferably methoxy,
(4) trifluoromethylthio,
(5) cyano,
(6) carboxy, or
(7) hydroxy.

A preferred group or compounds is that wherein $R^1$ is hydrogen.

Another preferred group of compounds is that wherein $R^1$, $R^3$ and $R^4$ are hydrogen.

Preferred definitions for $R^2$ are $C_{1-5}$ alkyl, especially methyl or ethyl, and hydroxyethyl.

Preferred definitions for R are hydrogen, $C_{1-5}$ alkyl or benzyl.

A preferred species is 5-methyl-10,11-dihydro-5H-dibenzo[a,d]cyclohepten-5,10-imine (which is referred to below as "MK-801") or a pharmaceutically acceptable salt thereof.

The administration in the novel method of treatment of this invention may conveniently be oral, rectal, or parenteral at a dosage level of, for example, about 0.01 to 50 mg/kg, preferably about 0.05 to 10 mg/kg and especially about 0.05 to 0.5 mg/kg/day and may be administered on a regimen of 1 to 4 times per day.

The pharmaceutical formulations comprising the NMDA receptor antagonists of this invention may conveniently be tablets, pills, capsules, powders, or granules for oral administration; sterile parenteral solutions or suspensions for parenteral adminstration; or as suppositories for rectal administration.

The compounds useful in the novel method of treatment of this invention bind with a high affinity and in a reversible and saturable manner to membranes from rat brain cortex. In addition these useful compounds potently and selectively block responses to NMDA in a brain slice from rate cortex, the antagonism apparently being non-competitive.

BINDING STUDIES

Binding of [$^3$H]-MK-801 to rat brain in vitro was conducted in a crude synaptosomal membrane fraction (P2) prepared from rat cerebral cortex according to a modified method of Hulme et al, *Molecular Pharmocology* 14, 737–750 (1978). A large number of excitatory and inhibitory drugs failed to displace [$^3$H]-MK-801 up to a concentration of $10^{-4}$M. However, analogs of MK-801 displaced the [$^3$H]-MK-801 binding in a dose-dependent manner as shown in Tables I, II and III.

TABLE II
Displacement Potencies of Analogs of MK-801

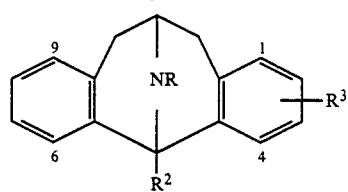

| Compound | R | $R^2$ | $R^3$ | Ki (μM) |
|---|---|---|---|---|
| L-639,420 | H | —CH$_2$CH$_3$ | H | 0.12 |
| L-638,204 | H | —CH$_3$ | H | 0.14 |
| L-637,686 | —CH$_3$ | —CH$_3$ | H | 1.20 |
| L-639,450 | H | H | 3-Cl | 0.15 |

TABLE III

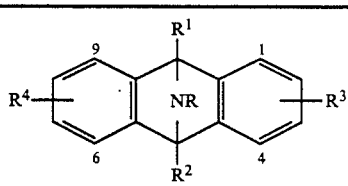

| Compound | R | $R^1$ | $R^2$ | $R^3$ | $R^4$ | Ki (μM) |
|---|---|---|---|---|---|---|
| L-633,239 | —CH$_3$ | —CH$_3$ | —CH$_3$ | 2-CN | H | 31.300 |
| L-633,170 | —(CH$_2$)$_2$CH$_3$ | —CH$_3$ | —CH$_3$ | H | H | 0.35 |
| L-631,922 | —CH$_3$ | —CH$_3$ | —CH$_3$ | 2-CF$_3$ | H | 109.400 |
| L-631,876 | —CH$_3$ | —CH$_3$ | H | H | H | 6.930 |
| L-627,891 | —CH$_3$ | —CH$_3$ | —CH$_3$ | H | H | 0.22 |

TABLE I
Displacement potencies of Analogs of MK-801

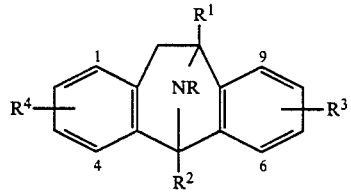

| Compound | R | $R^1$ | $R^2$ | $R^3$ | $R^4$ | Ki (μM) |
|---|---|---|---|---|---|---|
| L-640,689 | (+)H | H | —CH$_3$ | H | H | 0.04 |
| L-637,939 | H | H | —CH$_3$ | H | H | 0.56 |
| L-638,275 | —CH$_3$ | H | —CH$_3$ | H | H | 0.830 |
| L-638,276 | —CH$_3$ | H | H | H | H | 11.900 |
| L-639,015 | —CH$_2$CH=CH$_2$ | H | —CH$_3$ | H | H | 3.40 |
| L-639,057 | H | H | —CH$_2$CH$_3$ | H | H | 0.05 |
| L-639,442 | H | H | —CH$_3$ | 7-Br | H | 0.18 |
| L-639,470 | H | H | —(CH$_2$)$_2$CH$_3$ | H | H | 8.60 |
| L-639,902 | H | H | —CH$_2$CH$_2$OH | H | H | 0.26 |
| L-640,690 | (−) H | H | —CH$_3$ | H | H | 0.32 |
| L-641,042 | —CH$_2$CH$_2$OH | H | —CH$_3$ | H | H | 12.800 |
| L-641,074 | H | H | —CH$_3$ | H | 2-OCH$_3$ | 0.605 |
| L-641,086 | H | H | —CH$_3$ | 8-OCH$_3$ | H | 0.040 |
| L-641,285 | H | H | —CH$_3$ | 8-OH | H | 0.05 |
| L-641,368 | H | H | —CH$_3$ | 7-Cl | H | 0.08 |
| L-645,114 | —CH$_3$ | H | —CH$_3$ | H | H | 0.509 |
| L-645,156 | —(CH$_2$)$_2$CH$_3$ | H | —CH$_3$ | H | H | 0.450 |
| L-665,039 | H | H | —CH$_3$ | 7-OH | H | 0.02 |
| L-639,441 | H | H | —CH$_3$ | H | 3-Br | 0.02 |
| L-640,688 | —CH$_3$ | —CH$_3$ | —CH$_3$ | H | H | 0.71 |
| L-641,291 | H | H | —CH$_3$ | H | 2-OH | 0.34 |
| L-641,294 | H | H | —CH$_3$ | H | 3-Cl | 0.01 |

TABLE III-continued

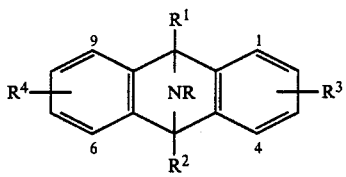

| Compound | R | R¹ | R² | R³ | R⁴ | Ki (μM) |
|---|---|---|---|---|---|---|
| L-632,938 | ▷ | —CH₃ | —CH₃ | H | H | 4.00 |
| L-633,744 | —(CH₂)₃CH₃ | —CH₃ | —CH₃ | H | H | 0.39 |

CORTICAL SLICE STUDIES

The effects of MK-801 and its analogs on responses to NMDA and quisqualate were assessed using the rat cortical slice as described by Harrison et al., *Brit. J. Pharmacol,* 84, 381–391 (1985). Cortical neurons in this preparation are depolarized by bath applications of NMDA. MK-801 produces a dose dependent depression of NMDA responses with a threshold dose of about 100 nM and complete suppression of responses at 1 μM. In contrast, responses to kainate and quisqualate are totally unaffected by MK-801 at doses of up to 30 μM.

The apparent potencies of MK-801 and its analogs are shown in Table IV; they correlate closely with results from [$^3$H]-MK-801 binding studies.

TABLE IV

| Compound | Apparent Potency as NMDA Antagonist Kb (μM) |
|---|---|
| L-640,689 (MK-801) | 0.08 |
| L-639,057 | 0.50 |
| L-641,285 | 0.10 |
| L-640,690 | 0.30 |
| L-627,891 | 1.13 |
| L-639,470 | 3.00 |
| L-637,686 | 2.00 |
| L-632,938 | 0.64 |
| L-633,170 | 0.30 |
| L-633,744 | 0.47 |
| L-637,939 | 0.09 |
| L-638,204 | 0.31 |
| L-639,015 | 3.10 |
| L-639,420 | 0.20 |
| L-639,441 | 1.00 |
| L-639,442 | 0.40 |
| L-639,902 | 0.20 |
| L-640,688 | 0.87 |
| L-641,291 | 0.51 |
| L-641,294 | 0.05 |
| L-641,368 | 1.00 |
| L-665,039 | 0.13 |

The responses to NMDA and quisqualate were examined on cortical slices from 4 rats which had been pretreated with MK-801 (1 mg/kg, i.p) 2 hours before they were sacrificed. Responses to NMDA were markedly depressed resulting in a shift to the right of the NMDA dose-response curve of approximately 2.4 fold when compared to the mean NMDA dose-response curved from untreated animals. The responses to quisqualate were much less affected with only the highest dose slightly depressed.

These results show that MK-801, when administered peripherally in reasonable doses, blocks NMDA receptor mediated events on central neurons.

NEUROPROTECTION STUDIES (a) Ischaemia was induced in gerbils by 10 or 30 minute unilateral occlusion of the carotid artery. Restoration of blood flow after occlusion was checked visually and the animals were allowed to survive for 4 days. The extent of neuronal degeneration in the hippocampus was assessed. Test animals were treated by administering MK-801 at doses of 1 and 10 mg/kg (i.p.) one hour prior to artery occulsion. The results are given in Table V.

TABLE V

|  | Control | 1 mg/kg MK-801 | 10 mg/kg MK-801 |
|---|---|---|---|
| (A) 10 min occlusion |  |  |  |
| Number of animals showing damage | 12 | 4 | 3 |
| Number undamaged | 8 | 11 | 12 |
| (B) 30 min occlusion |  |  |  |
| Number of animals surviving | 8 | 11 | 14 |
| Number dead | 7 | 4 | 1 |

(b) The right carotid artery of gerbils was occluded for 10 minutes and MK-801 at a dose of 1 mg/kg (i.p.) administered one hour before, then 1, 3, 5, 10 and 15 hours following occlusion. The animals were allowed to survive for 4 days and the extent of neuronal damage in the hippocampus was assessed. The results are given in Table VI.

TABLE VI

|  | Control | MK-801 - treated |
|---|---|---|
| Number of animals showing damage | 7 | 1 |
| Number undamaged | 1 | 8 |

(c) Ischaemia was induced in gerbils by 5 minute occlusion of both carotid arteries. Restoration of blood flow after occlusion was checked visually and the animals allowed to survive for 4 days. The extent of neuronal degeneration in the hippocampus was measured. Test animals were treated by administering MK-801 at doses of 1, 3 and 10 mg/kg (i.p.) one hour prior to occlusion. The results are given in Table VII

TABLE VII

|  | (No.) | Area of neuronal degeneration (mm²) | Percentage of anaimals with full protection |
|---|---|---|---|
| Control | (10) | 7.70 ± 0.25 | 0 |
| 1 mg/kg MK-801 | (5) | 0.47 ± 0.33 | 60 |
| 3 mg/kg MK-801 | (5) | 0.14 ± 0.16 | 80 |
| 10 mg/kg MK-801 | (10) | 0.84 ± 0.52 | 70 |

(d) The neuroprotective activity of compounds for use in accordance with the invention has also been determined by measuring the ability of the compounds to prevent increases in calcium levels in the gerbil hippocampus following bilateral artery occlusion. The results obtained are shown in Table VIII.

TABLE VII

| Compound | Depression of Hippocampal [Ca$^{2+}$] Relative Potency (MK-801 = 1) |
|---|---|
| MK-801 (L-640,689) | 1 (IC$_{50}$ ~ 0.1 mg/kg) |

TABLE VII-continued

| Compound | Depression of Hippocampal $[Ca^{2+}]$ Relative Potency (MK-801 = 1) |
|---|---|
| L-665,039 | 0.8 |
| L-641,291 | 1 |

What is claimed is:

1. A method of producing a neuroprotective effect by selectively antagonizing N-methyl-D-aspartate receptors which comprises the administration to a patient in need of such treatment, of an effective amount of a compound of structural formula:

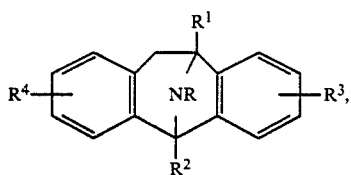

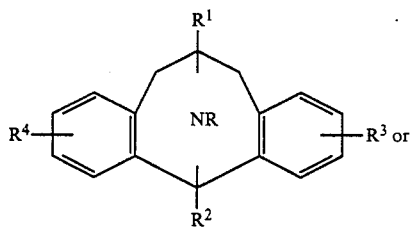

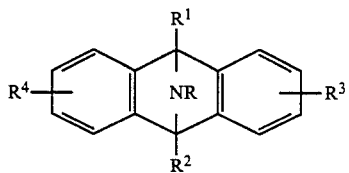

or a pharmaceutically acceptable salt thereof, wherein R is
  (1) hydrogen,
  (2) $C_{1-5}$alkyl,
  (3) $C_{2-5}$alkenyl,
  (4) (optionally substituted phenyl)-($C_{1-3}$alkyl),
  (5) $C_{3-6}$cycloalkyl,
  (6) ($C_{3-6}$cycloalkyl)-($C_{1-3}$alkyl), or
  (7) di($C_{1-5}$alkyl)amino-($C_{1-3}$alkyl);
$R^1$ is
  (1) hydrogen,
  (2) $C_{1-5}$alkyl,
  (3) $C_{2-5}$alkenyl,
  (4) phenyl-($C_{1-3}$alkyl),
  (5) $C_{3-6}$cycloalkyl, or
  (6) ($C_{3-6}$cycloalkyl)-($C_{1-3}$alkyl);
$R^2$ is
  (1) $C_{1-5}$alkyl,
  (2) $C_{1-5}$alkenyl,
  (3) phenyl-($C_{1-3}$alkyl),
  (4) ($C_{3-6}$cycloalkyl)-$C_{1-3}$alkyl),
  (5) di($C_{1-5}$alkyl)amino-$C_{1-5}$alkyl), or
  (6) ($C_{2-3}$hydroxyalkyl); and
$R^3$ and $R^4$ are independently,
  (1) hydrogen
  (2) halogen,
  (3) $C_{1-5}$alkoxy,
  (4) trifluoromethylthio,
  (5) cyano,
  (6) carboxy, or
  (7) hydroxy.

2. A method of producing a neuroprotective effect by selectively antagonizing N-methyl-D-aspartate receptors which comprises the administration to a patient in need of such treatment, of an effective amount of 5-methyl-10,11-dihydro-5H-dibenzo[a,d]-cyclohepten-5-10-imine or a pharmaceutically acceptable salt thereof.

3. The method according to claim 1, wherein $R^1$ is hydrogen.

4. The method according to claim 1, wherein $R^1$, $R^3$ and $R_4$ are hydrogen, R is hydrogen, $C_{1-5}$ alkyl, phenyl-$C_{1-3}$alkyl or chlorophenyl-$C_{1-3}$alkyl, and $R^2$ is $C_{1-5}$ alkyl or hydroxy-$C_{2-3}$ alkyl.

5. The method as described in claims 1, wherein the compounds are dextrorotatory.

6. The method as described in claim 3, wherein the compounds are dextrorotatory.

7. The method as described in claim 4, wherein the compounds are dextrorotatory.

8. The method as described in claim 2, wherein the compound is dextrorotatory.

* * * * *